United States Patent
Hares et al.

(10) Patent No.: US 12,414,825 B2
(45) Date of Patent: *Sep. 16, 2025

(54) SURGICAL ARM

(71) Applicant: CMR SURGICAL LIMITED, Cambridge (GB)

(72) Inventors: Luke David Ronald Hares, Milton (GB); Steven James Randle, Warwickshire (GB)

(73) Assignee: CMR SURGICAL LIMITED, Cambridge (GB)

( * ) Notice: Subject to any disclaimer, the term of this patent is extended or adjusted under 35 U.S.C. 154(b) by 355 days.

This patent is subject to a terminal disclaimer.

(21) Appl. No.: 17/543,325

(22) Filed: Dec. 6, 2021

(65) Prior Publication Data
US 2022/0087757 A1 Mar. 24, 2022

Related U.S. Application Data

(63) Continuation of application No. 15/910,302, filed on Mar. 2, 2018, now Pat. No. 11,224,488, which is a
(Continued)

(30) Foreign Application Priority Data
Mar. 7, 2014 (GB) .................................... 1404065

(51) Int. Cl.
*B25J 9/06* (2006.01)
*A61B 34/30* (2016.01)

(52) U.S. Cl.
CPC ........ *A61B 34/30* (2016.02); *A61B 2034/305* (2016.02); *B25J 9/06* (2013.01)

(58) Field of Classification Search
CPC ...... A61B 34/30; A61B 2034/305; B25J 9/06; B25J 9/065
See application file for complete search history.

(56) References Cited

U.S. PATENT DOCUMENTS 4,283,764 A * 8/1981 Crum .................... G05B 19/427
318/568.22
4,308,584 A * 12/1981 Arai ....................... G05B 19/41
414/730
(Continued)

FOREIGN PATENT DOCUMENTS

CN 101106952 1/2008
CN 101927498 A 12/2010
(Continued)

OTHER PUBLICATIONS

Notification of Reasons for Refusal dated Nov. 25, 2019 issued in Japanese Patent Application No. 2018-243117. (3 pages).
(Continued)

*Primary Examiner* — William C Joyce
(74) *Attorney, Agent, or Firm* — ROTHWELL, FIGG, ERNST & MANBECK, P.C.

(57) ABSTRACT

A surgical robot comprising an articulated arm, the arm having a terminal portion comprising: a distal segment having an attachment for a surgical instrument; an intermediate segment; and a basal segment whereby the terminal portion is attached to the remainder of the arm; a first articulation between the distal segment and the intermediate segment, the first articulation permitting relative rotation of the distal segment and the intermediate segment about a first axis; and a second articulation between the intermediate segment and the basal segment, the second articulation permitting relative rotation of the intermediate segment and the basal segment about a second axis; wherein: the intermediate segment comprises a third articulation permitting relative rotation of the distal segment and the basal segment about third and fourth axes; and the first, second and third articulations are arranged such that in at least one configuration of the third articulation the first and second axes are
(Continued)

parallel and the third and fourth axes are transverse to the first axis.

18 Claims, 7 Drawing Sheets

Related U.S. Application Data continuation of application No. 15/024,291, filed as application No. PCT/GB2014/053523 on Nov. 28, 2014, now Pat. No. 9,937,012.

(56) References Cited

U.S. PATENT DOCUMENTS

| | | | |
|---|---|---|---|
| 4,739,241 A | 4/1988 | Vachtsevanos et al. | |
| 4,805,477 A | 2/1989 | Akeel | |
| 4,878,393 A | 11/1989 | Duta et al. | |
| 4,911,033 A | 3/1990 | Rosheim et al. | |
| 4,975,856 A | 12/1990 | Vold et al. | |
| 5,036,724 A | 8/1991 | Rosheim | |
| 5,239,883 A | 8/1993 | Rosheim | |
| 5,428,713 A | 6/1995 | Matsumaru | |
| 5,697,256 A | 12/1997 | Matteo | |
| 5,737,500 A | 4/1998 | Seraji et al. | |
| 5,740,699 A | 4/1998 | Ballantyne et al. | |
| 5,828,813 A | 10/1998 | Ohm | |
| 6,676,684 B1 | 1/2004 | Morley et al. | |
| 6,699,177 B1 | 3/2004 | Wang et al. | |
| 7,121,781 B2 | 10/2006 | Sanchez | |
| 8,271,137 B2 | 9/2012 | Moon et al. | |
| 8,394,082 B2 | 3/2013 | Okamoto et al. | |
| 8,423,190 B1 | 4/2013 | Yasuda et al. | |
| 8,442,686 B2 | 5/2013 | Saito et al. | |
| 8,977,392 B2 | 3/2015 | Nammoto et al. | |
| 9,119,653 B2 | 9/2015 | Amat Girbau et al. | |
| 9,317,032 B2 | 4/2016 | Finkemeyer | |
| 2003/0065310 A1 | 4/2003 | Wang et al. | |
| 2003/0083648 A1 | 5/2003 | Wang et al. | |
| 2003/0100892 A1 | 5/2003 | Morley et al. | |
| 2003/0167061 A1 | 9/2003 | Schlegel et al. | |
| 2004/0115606 A1* | 6/2004 | Davies | A63B 69/0057 434/258 |
| 2007/0120512 A1 | 5/2007 | Albu-Schaffer et al. | |
| 2007/0151391 A1 | 7/2007 | Larkin et al. | |
| 2008/0019533 A1 | 1/2008 | Noguchi et al. | |
| 2010/0011899 A1* | 1/2010 | Kim | B25J 15/0009 74/490.06 |
| 2011/0071677 A1 | 3/2011 | Stilman | |
| 2011/0087238 A1 | 4/2011 | Wang et al. | |
| 2011/0106303 A1* | 5/2011 | Lim | B62D 57/032 901/1 |
| 2011/0144659 A1 | 6/2011 | Sholev | |
| 2011/0172823 A1 | 7/2011 | Kim et al. | |
| 2013/0131695 A1 | 5/2013 | Scarfogliero et al. | |
| 2014/0005662 A1 | 1/2014 | Shelton | |
| 2014/0283642 A1 | 9/2014 | Harada et al. | |
| 2014/0371762 A1 | 12/2014 | Farritor et al. | |
| 2015/0100066 A1 | 4/2015 | Kostrzewski et al. | |
| 2015/0202015 A1 | 7/2015 | Elhawary et al. | |
| 2016/0104283 A1 | 4/2016 | Fujiwara et al. | |
| 2016/0129588 A1 | 5/2016 | Pfaff | |
| 2018/0161115 A1 | 6/2018 | Farritor et al. | |
| 2020/0330172 A1 | 10/2020 | Farritor et al. | |

FOREIGN PATENT DOCUMENTS

| | | |
|---|---|---|
| CN | 102186396 A | 9/2011 |
| CN | 202146362 U | 2/2012 |
| CN | 102892363 A | 1/2013 |
| CN | 104057465 A | 9/2014 |
| CN | 104349742 A | 2/2015 |
| CN | 106102630 A | 11/2016 |
| CN | 110680504 A | 1/2020 |
| EP | 2252231 A2 | 11/2010 |
| EP | 2 252 231 B1 | 10/2019 |
| JP | H04502584 A | 5/1992 |
| JP | H0732286 A | 2/1995 |
| JP | 2000505328 A | 5/2000 |
| JP | 2001-145634 A | 5/2001 |
| JP | 2009-165504 | 7/2009 |
| JP | 2010-155335 A | 7/2010 |
| JP | 2011-530373 A | 12/2011 |
| JP | 2012-527276 A | 11/2012 |
| JP | 2013-94920 A | 5/2013 |
| WO | 0203878 A1 | 1/2002 |
| WO | WO 2002/03878 A1 | 1/2002 |
| WO | WO 2006/079108 | 7/2006 |
| WO | 2010/007837 A1 | 1/2010 |
| WO | 2010/055745 A1 | 5/2010 |
| WO | WO 2010/140844 A2 | 12/2010 |
| WO | 2011/060315 A2 | 5/2011 |
| WO | 2012/007014 A1 | 1/2012 |
| WO | WO 2013/154157 A1 | 10/2013 |
| WO | 2015132549 A1 | 9/2015 |

OTHER PUBLICATIONS

I-Stitch, A.M.I., Product Group Urogynaecology, Dec. 2013 (2 pages).
Hyosig Kang et al., "Autonomous Suturing using Minimally Invasive Surgerical Robots", IEEE International Conference on Control Applications, Anchorage, Alaska, USA, Sep. 25-27, 2000 (6 pages).
Extended European Search Report dated Oct. 12, 2021 in related European Patent Application No. 21175213.4 (8 pages total).
Indian Office Action with English translation dated Jan. 12, 2022 in related Indian Application No. 202018053666 (6 pages total).
Adnan,S., Design, Analysis, Implementation, and Control of a Mobile Robotic Testbed for Telepresence (Mar. 1992) (unpublished Ph.D. dissertation, Rice University).
Chinese Patent Application No. 201480076954.9, Office Action dated Jun. 28, 2018.
Chinese First Office Action dated Oct. 25, 2023 in Chinese Application No. 202011071694.X (10 pages).
Chinese Notice of Allowance with English translation dated Jul. 25, 2024 in related Chinese Application No. 202011071694.X (7 pages).

* cited by examiner

SURGICAL ARM

REFERENCE TO RELATED APPLICATION

This application is a continuation of U.S. patent application Ser. No. 15/910,302, filed Mar. 2, 2018, which is a continuation of U.S. patent application Ser. No. 15/024,291, filed Mar. 23, 2016, entitled "Surgical Arm," now U.S. Pat. No. 9,937,012, which is a U.S. national phase under 35 U.S.C. § 371 of International Patent Application No. PCT/GB2014/053523, filed Nov. 28, 2014, entitled "Surgical Arm," which claims priority to United Kingdom Patent Application No. 1404065.3, filed Mar. 7, 2014, the entirety of each of which is hereby incorporated by reference herein.

DESCRIPTION

This invention relates to robots for performing surgical tasks.

Various designs of robot have been proposed for performing or assisting in surgery. However, many robot designs suffer from problems that make them unsuitable for performing a wide range of surgical procedures. A common reason for this is that in order for a surgical robot to work well in a wide range of surgical situations it must successfully balance a set of demands that are particular to the surgical environment.

Normally a surgical robot has a robot arm, with a surgical instrument attached to the distal end of the robot arm.

A first common demand on a surgical robot is that its robot arm should offer sufficient mechanical flexibility to be able to position the surgical instrument in a wide range of locations and orientations so that the working tip of the surgical instrument (the end effector) can reach a range of desired surgical sites. This demand alone could easily be met by a conventional fully flexible robot arm with six degrees of freedom, as illustrated in FIG. 1. However, secondly, a surgical robot must also be capable of positioning its arm such that the end effector of the instrument is positioned very accurately without the robot being excessively large or heavy. This requirement arises because unlike the large-scale robots that are used for many other tasks, (a) surgical robots need to work safely in close proximity to humans: not just the patient, but typically also surgical staff such as anaesthetists and surgical assistants, and (b) in order to perform many laparoscopic procedures it is necessary to bring multiple end effectors together in close proximity, so it is desirable for surgical robot arms to be small enough that they can fit closely together. Another problem with the robot of FIG. 1 is that in some surgical environments there is not sufficient space to be able to locate the base of the robot in a convenient location near the operating site.

Many robots have a wrist (i.e. the terminal articulated structure of the arm) which comprises two joints that permit rotation about axis generally along the arm ("roll joints") and between them one joint that permits rotation about an axis generally transverse to the arm (a "pitch joint"). Such a wrist is shown in FIG. 2, where the roll joints are indicated as 1 and 3 and the pitch joint is indicated as 2. With the wrist in the configuration shown in FIG. 2 the axes of the joints 1 to 3 are indicated as 4 to 6 respectively. This wrist gives an instrument 7 the freedom of movement to occupy a hemisphere whose base is centred on axis 4. However, this wrist is not well suited for use in a surgical robot. One reason for this is that when the pitch joint 2 is offset by just a small angle from the straight position shown in FIG. 2 a large rotation of joint 1 is needed to produce some relatively small lateral movements of the tip of the instrument. In this condition, when the pitch joint is almost straight, in order to move the end effector smoothly in a reasonable period of time the drive to joint 1 must be capable of very fast operation. This requirement is not readily compatible with making the arm small and lightweight because it calls for a relatively large drive motor and a sufficiently stiff arm that the motor can react against it without jolting the position of the arm.

There is a need for a robot arm that can successfully perform a wider range of surgical procedures than existing arms.

According to one aspect of the present invention there is provided a surgical robot comprising an articulated arm, the arm having a terminal portion comprising: a distal segment having an attachment for a surgical instrument; an intermediate segment; and a basal segment whereby the terminal portion is attached to the remainder of the arm; a first articulation between the distal segment and the intermediate segment, the first articulation permitting relative rotation of the distal segment and the intermediate segment about a first axis; and a second articulation between the intermediate segment and the basal segment, the second articulation permitting relative rotation of the intermediate segment and the basal segment about a second axis; wherein: the intermediate segment comprises a third articulation permitting relative rotation of the distal segment and the basal segment about third and fourth axes; and the first, second and third articulations are arranged such that in at least one configuration of the third articulation the first and second axes are parallel and the third and fourth axes are transverse to the first axis.

In the said configuration the third and fourth axes may be perpendicular to the first axis.

In the said configuration the first and second axes may be collinear.

The third and fourth axes intersect each other, either in all configurations of the arm or in some configurations.

The third and fourth axes may be perpendicular to each other, either in all configurations of the arm or in some configurations.

The first articulation may be a revolute joint. The second articulation may be a revolute joint. The third articulation may be a spherical joint or a pair of revolute joints. The third articulation may, for example, be a universal joint (i.e. a Cardan joint), a constant velocity joint, a ball joint or a double-hinge joint in which the hinge axes are transverse to each other. If the third articulation is a universal joint the axes of the universal joint may intersect or may be offset.

In one arrangement the only means of articulating the attachment for a surgical instrument relative to the basal segment may be the first, second and third articulations. In other embodiments there may be additional revolute or translational joints.

The attachment for a surgical instrument may be located on the first axis, either in all configurations of the arm or in some configurations. The attachment for the surgical instrument may be capable of transmitting there through motive force for causing one or more joints in the surgical instrument to articulate independently of motion of the arm. The surgical instrument may be a laparoscopic and/or arthroscopic instrument. The surgical robot may be a laparoscopic and/or arthroscopic robot.

The surgical robot may comprise a surgical instrument attached to the attachment. The surgical instrument may extend in a direction substantially along the first axis, either in all configurations of the arm or in some configurations.

According to a second aspect of the present invention there is provided a surgical robot as claimed in any preceding claim, wherein the arm comprises: a base; and a proximal portion extending between the base and the basal segment of the terminal portion of the arm, the proximal portion being articulated along its length and being rigidly connected to the basal segment.

The proximal portion may comprise: a first arm segment; a second arm segment coupled to the first arm segment by a first arm articulation whereby the second arm segment can rotate relative to the first arm segment about a first arm axis; a third arm segment coupled to the second arm segment by a second arm articulation whereby the third arm segment can rotate relative to the second arm segment about a second arm axis; a fourth arm segment coupled to the third arm segment by a third arm articulation whereby the fourth arm segment can rotate relative to the third arm segment about a third arm axis; and a fifth arm segment coupled to the fourth arm segment by a fourth arm articulation whereby the fifth arm segment can rotate relative to the fourth arm segment about a fourth arm axis; wherein the second arm axis is transverse to the first arm axis, the third arm axis is transverse to the second arm axis and the fourth arm axis is transverse to the third arm axis; and the second and third arm segments together form an elongate limb that extends in a direction along the third arm axis.

The second arm axis is perpendicular to the first arm axis, either in all configurations of the arm or in some configurations The third arm axis may be perpendicular to the second arm axis, either in all configurations of the arm or in some configurations The fourth arm axis may be perpendicular to the third arm axis, either in all configurations of the arm or in some configurations The first arm segment may be rigidly attached to the base.

Each of the first, second, third and fourth arm articulations may be a revolute joint. In one arrangement the only means of articulating the fifth arm segment relative to the base can be the first, second, third and fourth arm articulations.

The surgical robot may have a first additional articulation between the first arm segment and the base. The first additional articulation may permit relative rotation of the first arm segment and the base about a first additional axis transverse to the first arm axis.

The surgical robot may have a second additional articulation between the first arm segment and the base. The second additional articulation may permit relative rotation of the first arm segment and the base about a second additional axis transverse to the first additional axis.

The second arm segment may comprise a third additional articulation whereby the second arm segment can flex about an axis transverse to the third arm axis.

The second arm axis may be offset from the first arm axis in a direction perpendicular to the first arm axis, either in all configurations of the arm or in some configurations.

The second arm axis may be offset from the third arm axis in a direction perpendicular to the third arm axis, either in all configurations of the arm or in some configurations.

The fourth arm axis may be offset from the third arm axis in a direction perpendicular to the third arm axis, either in all configurations of the arm or in some configurations.

The base may be arranged such that the first axis is fixedly offset from vertical by at least 20°.

The fifth arm segment may be rigidly attached to the basal segment of the terminal portion of the arm.

The fifth arm segment and the basal segment may together form an elongate limb that extends in a direction along the second axis.

The second axis may be transverse to the fourth arm axis. The second axis may be perpendicular to the fourth arm axis, either in all configurations of the arm or in some configurations.

The fourth arm axis may be offset from the second axis in a direction perpendicular to the second axis.

The arm may comprise eight revolute joints by means of which the distal end of the arm may be rotated relative to the proximal end of the arm. The eight revolute joints may provide the distal end of the arm with six degrees of freedom relative to the proximal end of the arm.

According to a third aspect of the invention there is provided a surgical robot comprising: a base; and an arm extending from the base and terminating at its distal end in a wrist having thereon an attachment for a surgical instrument; wherein: the arm is articulated by a series of revolute joints along its length, the arm joints comprising, in order running from the base: i. a first joint having a first axis; ii. a second joint having a second axis transverse to the first axis; iii. a third joint having a third axis transverse to the second axis; and iv. a fourth joint having a fourth axis transverse to the third axis; and the wrist is articulated by a second series of revolute joints along its length, the joints of the wrist comprising, in order running towards the attachment: v. a fifth joint having a fifth axis; vi. a sixth joint having a sixth axis transverse to the fifth axis; and vii. a seventh joint having a seventh axis transverse to both the fifth and sixth axes.

The fifth and sixth axes may intersect, either in all configurations of the arm or in some configurations.

The first to seventh joints may be the only means of articulation of the arm.

The wrist may comprise an eighth revolute joint between the fifth joint and the fourth joint. The axis of the eighth joint may be transverse to both the fifth and sixth axes.

In one configuration of the fifth and sixth joints the eighth axis and the seventh axis may be parallel.

In one configuration of the fifth and sixth joints the eighth axis and the seventh axis may be collinear.

The first to eighth joints may be the only means of articulation of the arm.

The surgical robot may comprise a first additional revolute joint between the first joint and the base. The first additional joint may have a first additional axis perpendicular to the first axis.

The surgical robot may comprise a second additional revolute joint between the first additional revolute joint and the base. The second additional revolute joint may have a second additional axis perpendicular to the first additional axis.

The surgical robot may comprise a third additional revolute joint between the second joint and the third joint. The third additional joint may have an axis transverse to the first axis.

The axis of the third additional joint may be parallel to the second axis.

The third articulation or the fifth and sixth joints may be constituted by a joint structure having an intermediate member capable of moving about a first spherical joint with respect to the basal segment and about a second spherical joint with respect to the distal segment, the first and second spherical joints being constrained to move in a plane with respect to the intermediate member.

The joint structure may have a follower captive within the intermediate member and coupled by the first and second spherical joints to the basal segment and the distal segment respectively, the follower being constrained to move linearly with respect to the intermediate member.

The surgical robot may comprise a plurality of linear actuators arranged between the basal segment and the intermediate member for causing relative rotation of the distal segment and the basal segment about third and fourth axes.

The present invention will now be described by way of example with reference to the accompanying drawings. In the drawings.

Figure 8A:
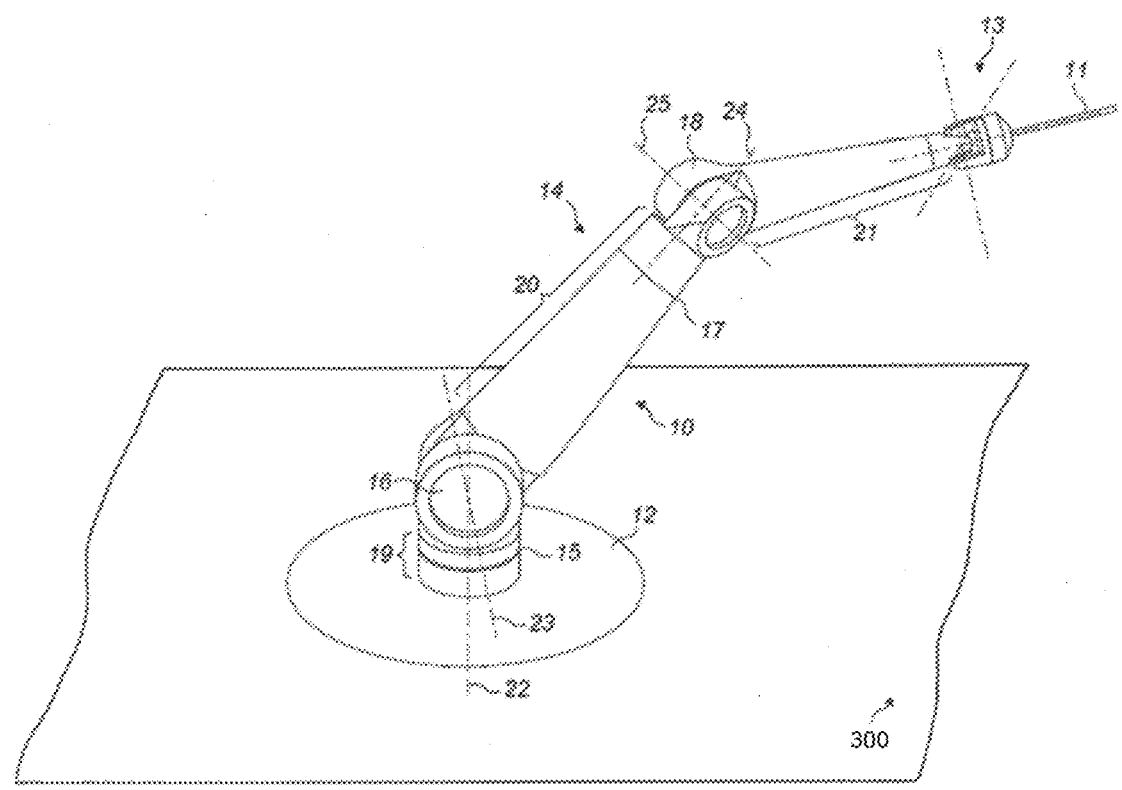
Figure 8B:
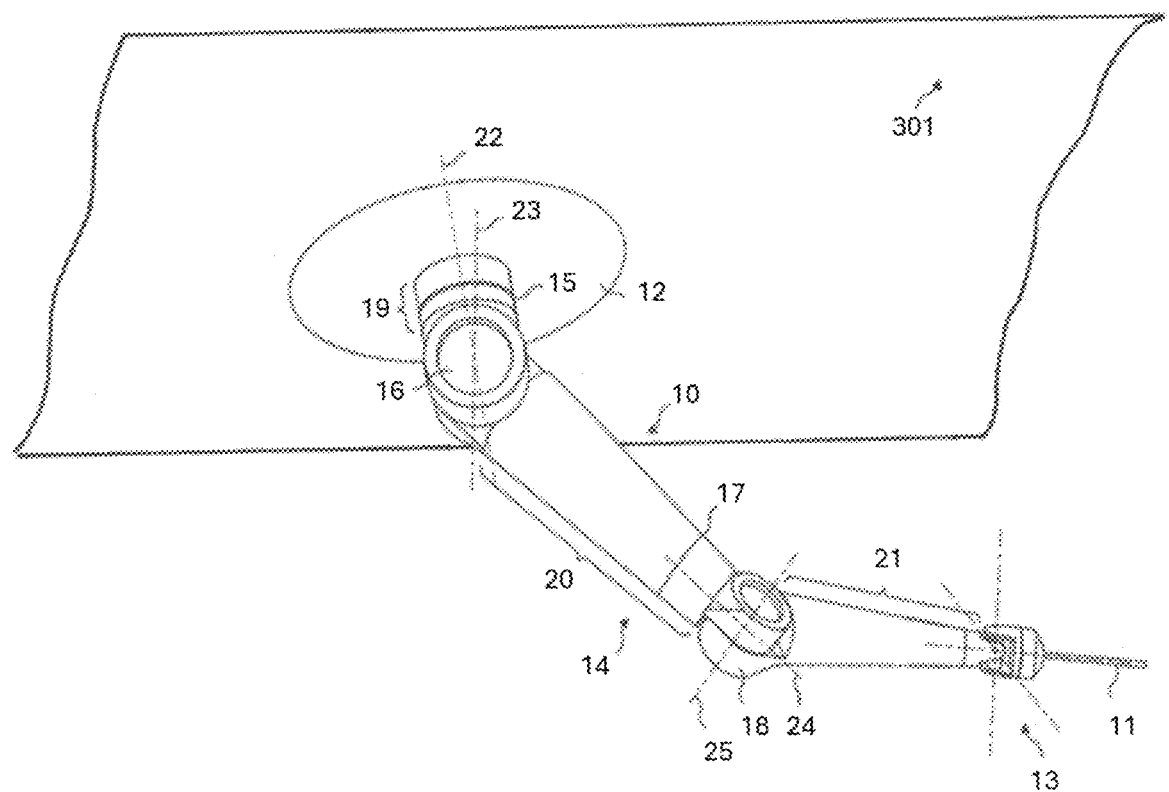
Figure 8C:
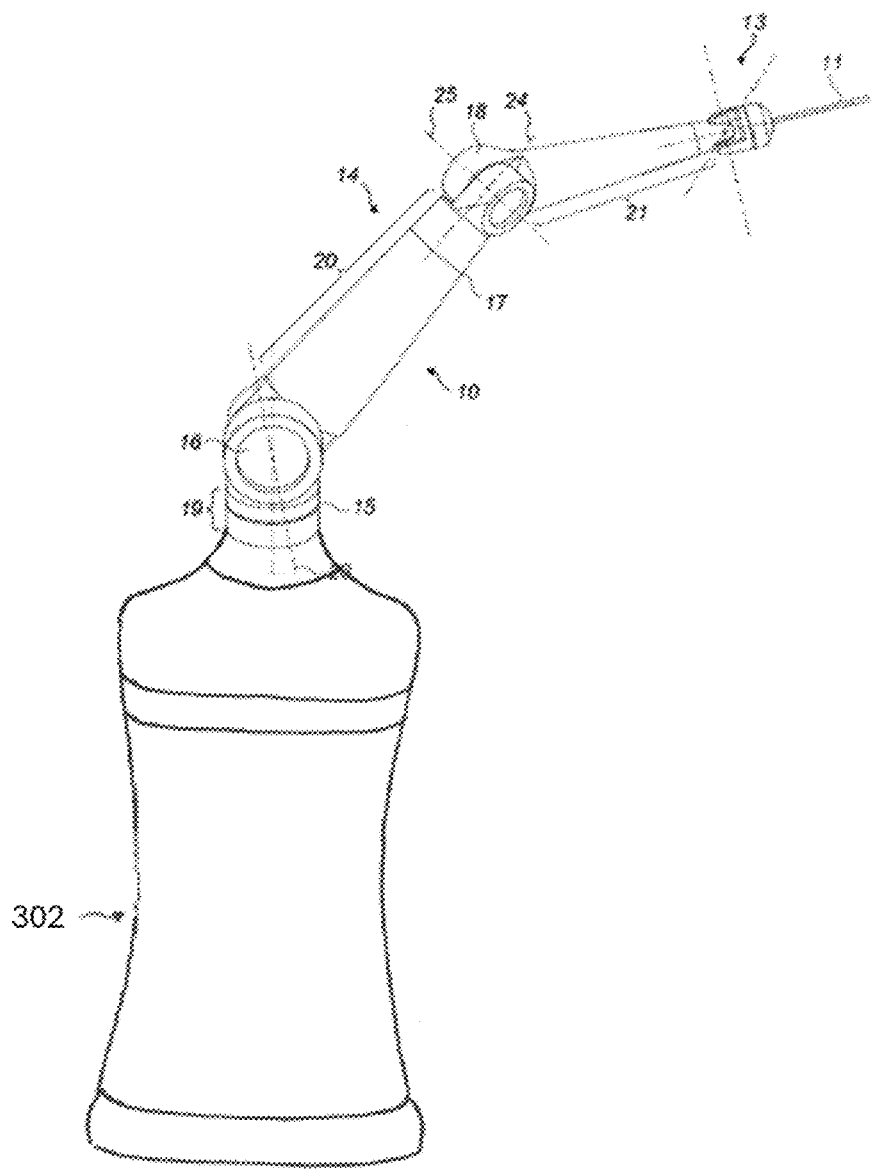

FIGS. 8a, 8b, and 8c show a robot arm mounted to a floor, a ceiling, and a trolley or cart, respectively.

Figure 1:
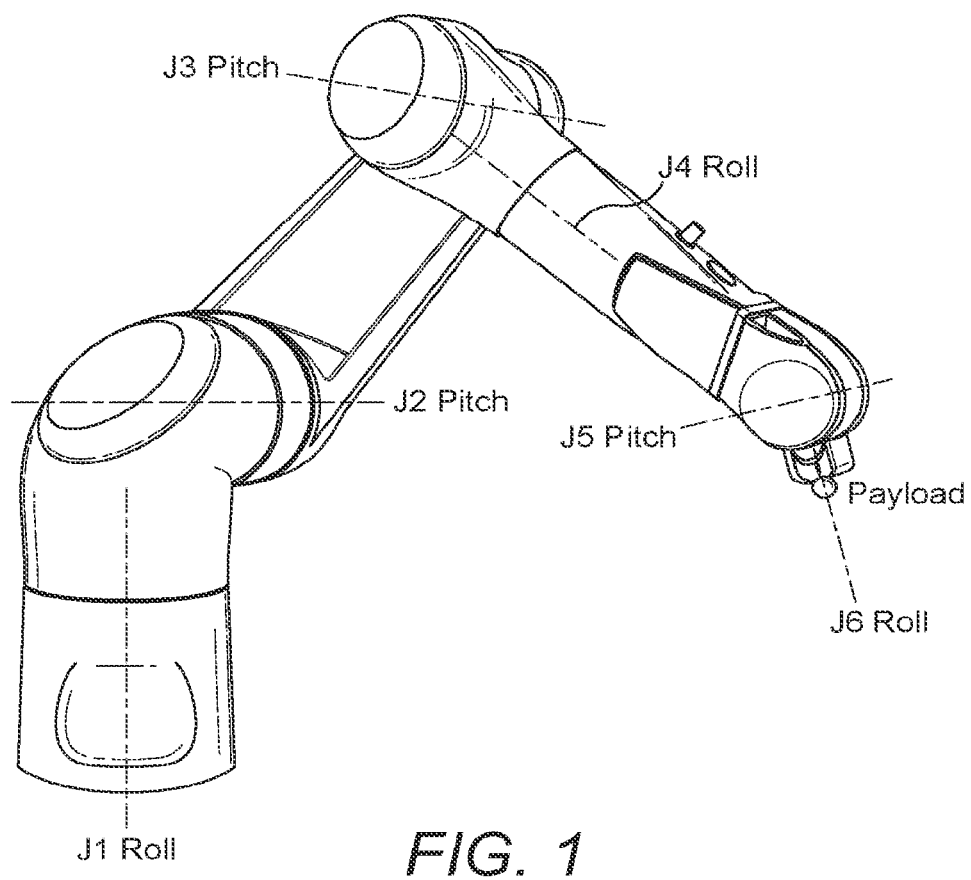
FIG. 1 shows a prior art robot arm.
Figure 2:
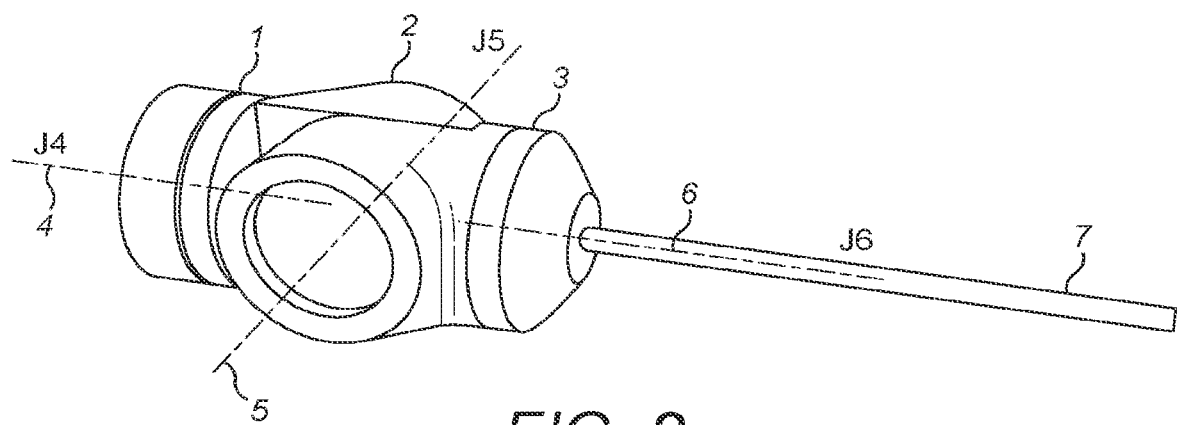
FIG. 2 shows a prior art robot wrist.
Figure 3:
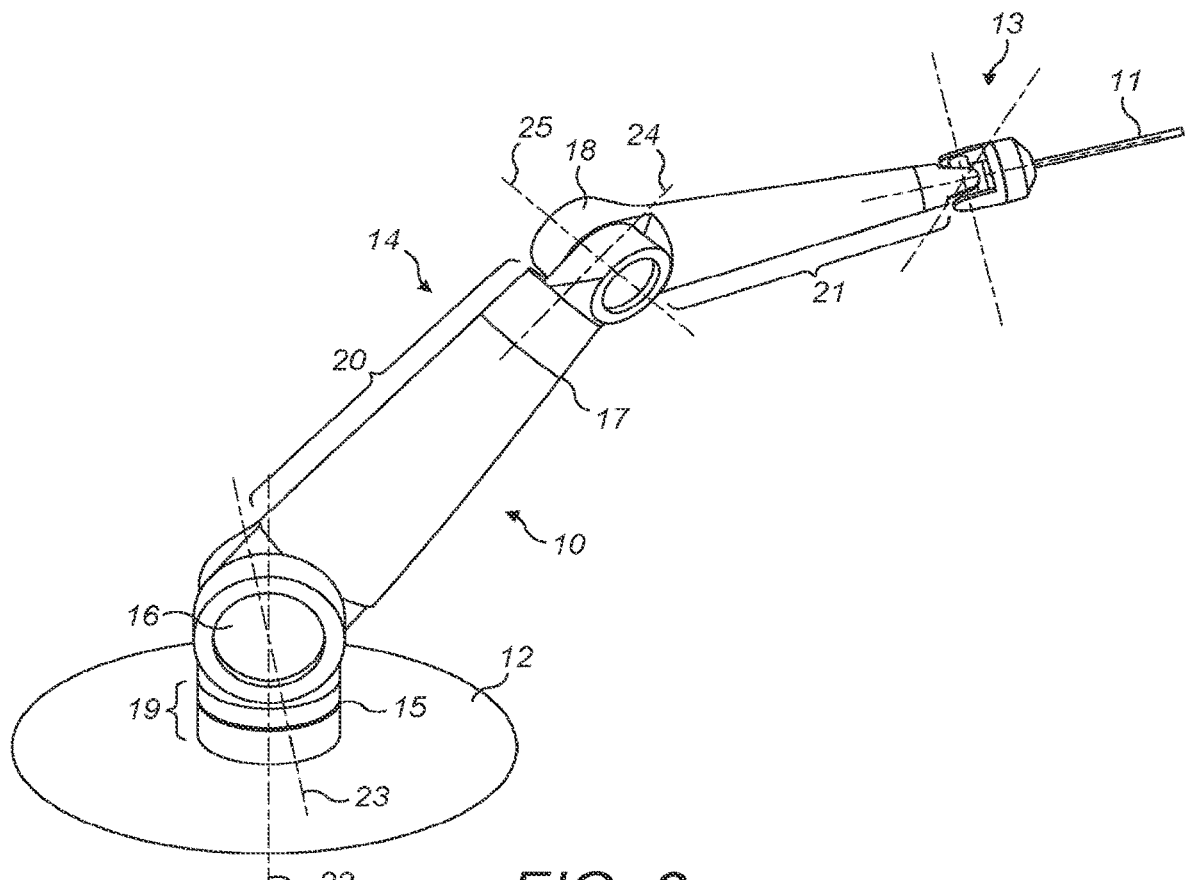
FIG. 3 shows a robot arm according to an embodiment of the present invention having a surgical instrument attached thereto.
Figure 4A:
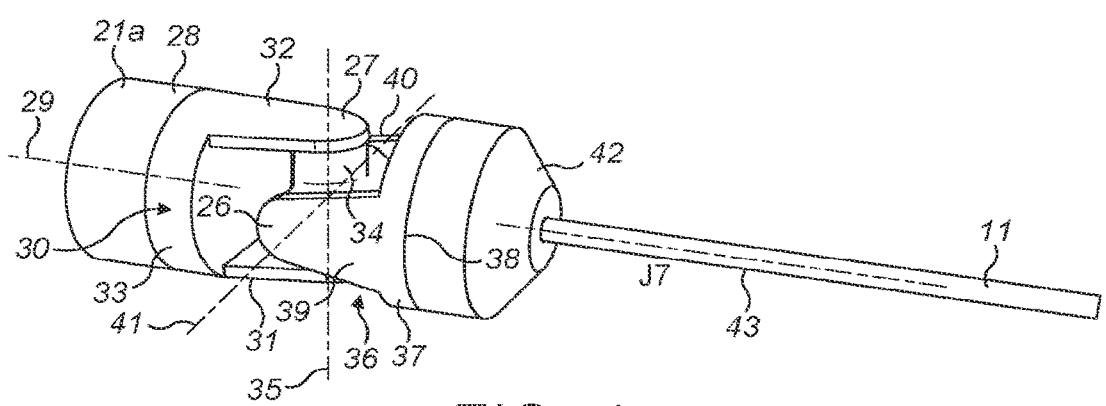
FIG. 4 shows the wrist of the arm of FIG. 2. The wrist is illustrated in three different configurations at FIGS. 4a, 4b and 4c.
Figure 4B:
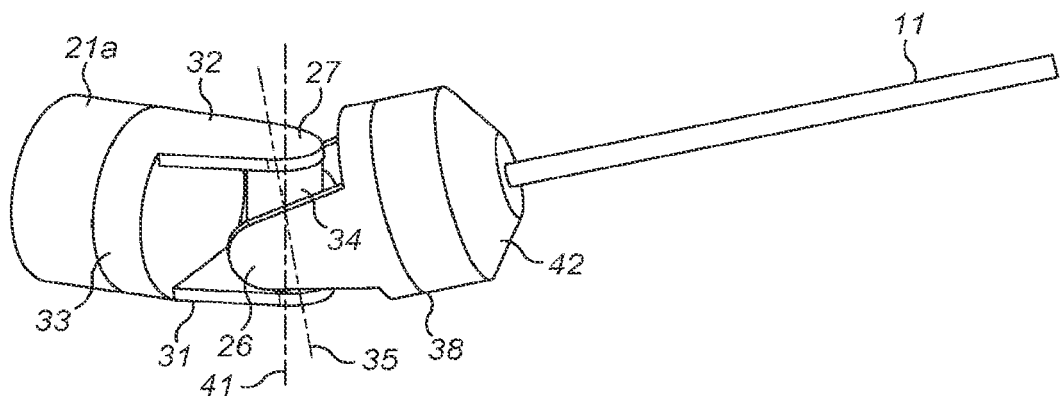
Figure 4C:
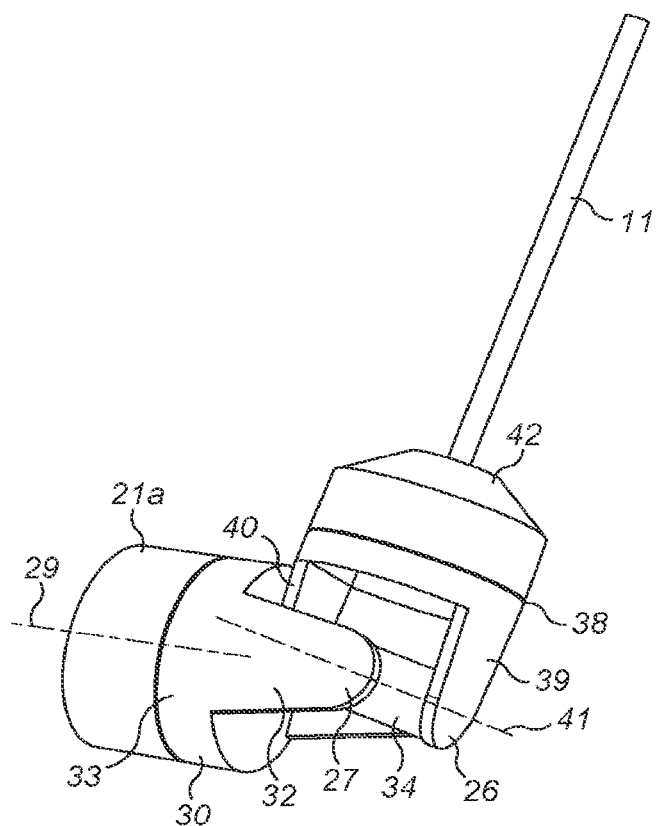

The surgical robot arm of FIGS. 3 and 4 has a wrist in which two joints that permit rotation about axes generally transverse to the distal portion of the arm are located between two joints that permit rotation about axes generally parallel to the distal portion of the arm. This arrangement permits the instrument to move in a hemispherical space whose base is centred on the distal part of the arm, but without requiring high-speed motion of one of the joints in order to move the end effector smoothly, and without requiring motion of any of the other parts of the arm.

In more detail, FIG. 3 shows a robot arm (indicated generally at 10) having a surgical instrument 11 attached thereto. The robot arm extends from a base 12. The base could be mounted to the floor 300 of an operating theatre (FIG. 8a), or to a fixed plinth, could be part of a mobile trolley or cart 302 (FIG. 8c), could be mounted to a bed or could be mounted to the ceiling 301 of an operating room (FIG. 8b). The base is fixed in place relative to the patient's bed or chair when an operation is being carried out. The robot arm comprises a wrist portion shown generally at 13 and a main portion shown generally at 14. The main portion makes up the majority of the extent of the arm and terminates at its distal end in its attachment to the wrist portion. The proximal end of the main portion is attached to the base. The wrist portion makes up the distal part of the arm and is attached to the distal end of the main portion.

The main portion of the arm comprises four joints 15, 16, 17, 18 and three shaft sections 19, 20, 21. The joints are revolute joints. The shaft sections are rigid, with the exception of joints 15 and 17 which are set into shaft sections 19 and 20 respectively. Each shaft section may have substantial length, and serve to provide the arm with reach and the ability to offset the wrist laterally and/or vertically from the base. The first shaft section could be truncated relative to the second and third shaft sections if the base is located in a suitable place; particularly if the base is elevated from the floor.

The first shaft section 19 is attached to the base 12. In practice the first shaft section can conveniently extend in a generally upright direction from the base but it could extend at a significant incline to vertical, or even horizontally.

Joint 15 is located in the first shaft section. Joint 15 permits relative rotation of the proximal part of the first shaft section, which is fixed to the base, and the remainder of the arm about an axis 22. Conveniently, axis 22 is parallel with or substantially parallel with the main extent of the first shaft section in forming the arm, which runs from the base towards joint 16. Thus, conveniently the angle of axis 22 to the main extent of the first shaft section in forming the arm could be less than 30°, less than 20° or less than 10°. Axis 22 could be vertical or substantially vertical. Axis 22 could extend between the base and joint 16.

Joint 16 is located at the distal end of the first shaft section 19. Joint 16 permits relative rotation of the first shaft section 19 and the second shaft section 20, which is attached to the distal end of joint 16, about an axis 23 which is transverse to the first shaft section 19 and/or the second shaft section 20. Conveniently axis 23 is perpendicular or substantially perpendicular to either or both of the first and second shaft sections. Thus, conveniently the angle of axis 23 to the main extents of either or both of the first and second shaft sections could be less than 30°, less than 20° or less than 10°. Conveniently axis 23 is perpendicular or substantially perpendicular to axis 22 and/or to the axis 24 to be described below.

Joint 17 is located in the second shaft section. Joint 17 permits relative rotation of the proximal part of the second shaft section and the remainder of the arm about an axis 24. Conveniently, axis 24 is parallel with or substantially parallel with the main extent of the second shaft section. Thus, conveniently the angle of axis 24 to the main extent of the second shaft section could be less than 30°, less than 20° or less than 10°. Axis 24 could intersect or substantially intersect (e.g. within 50 mm of) axis 23 and the axis 25 that will be described below. In FIG. 3 joint 17 is shown located closer to the distal end of the second shaft section than the proximal end. This is advantageous because it reduces the mass that needs to be rotated at joint 17, but joint 17 could be located at any point on the second shaft section. The second shaft section is conveniently longer than the first shaft section.

Joint 18 is located at the distal end of the second shaft section 20. Joint 18 permits relative rotation of the second shaft section and the third shaft section 21, which is attached to the distal end of joint 18, about an axis 25 which is transverse to the second shaft section 20 and/or the third shaft section 21. Conveniently axis 25 is perpendicular or substantially perpendicular to either or both of the second and third shaft sections. Thus, conveniently the angle of axis 25 to the main extents of either or both of the second and third shaft sections could be less than 30°, less than 20° or less than 10°. Conveniently axis 25 is perpendicular or substantially perpendicular to axis 24 and/or to the axis 29 to be described below.

In summary, then, in one example the main portion of the arm can be composed as follows, in order from the base to the distal end of the main portion:

1. a first shaft section 19 having substantial or insubstantial length and containing a joint 15 that permits rotation e.g. about an axis generally along the extent (if any) of the first shaft section in forming the arm (a "roll joint");
2. a joint 16 permitting rotation transverse to the first shaft section and/or to the axis of the preceding joint (joint 15) and/or to the axis of the succeeding joint (joint 17) (a "pitch joint");
3. a second shaft section 20 having substantial length and containing a joint 17 that permits rotation about an axis generally along the extent of the second shaft section and/or to the axis of the preceding joint (joint 16) and/or to the succeeding joint (joint 18) (a roll joint);

4. a joint 18 permitting rotation transverse to the second shaft section and or to the preceding joint (joint 17) and/or to the succeeding joint (joint 28) (a pitch joint); and 5. a third shaft section 21 having substantial length.

The wrist portion 13 is attached to the distal end of the third shaft section. The wrist portion is shown in more detail in FIG. 4. In FIG. 4, 4a shows the wrist in a straight configuration, 4b shows the wrist in a bent configuration from movement at a joint 26 and 4c shows the wrist in a bent configuration from movement at a joint 25. Like parts are indicated by the same references in FIGS. 3 and 4. The straight configuration represents the mid-point of the motions of the transverse joints (26, 27) of the wrist.

The distal part of the third shaft section is designated 21a in FIG. 4. The wrist is attached to the distal end of the third shaft section by a joint 28. Joint 28 is a revolute joint which permits the wrist to rotate relative to the distal end of the arm about an axis 29. Conveniently, axis 29 is parallel with or substantially parallel with the main extent of the third shaft section. Thus, conveniently the angle of axis 29 to the main extent of the third shaft section could be less than 30°, less than 20° or less than 10°. Axis 29 could intersect or substantially intersect (e.g. within 50 mm) axis 25. Axis 29 is conveniently transverse to axis 25.

The proximal end of the wrist is constituted by a wrist base block 30. The wrist base block 30 is attached to joint 28. Wrist base block 30 abuts the distal end of the third shaft section 21. The wrist base block is rigid and comprises a base 33, by which it is attached to joint 28. The wrist base block also comprises a pair of spaced apart arms 31, 32 which extend from the base 33 of the wrist base block in a direction away from the third shaft section. An intermediate member 34 is pivotally suspended between the arms 31, 32 in such a way that it can rotate relative to the arms 31, 32 about an axis 35. This constitutes a revolute joint 27 of the wrist. The intermediate member 34 is conveniently in the form of a rigid block which may be of cruciform shape. A wrist head block 36 is attached to the intermediate member 34. The wrist head block is rigid and comprises a head 37 by which it is attached to a joint 38 to be described below, and a pair of spaced apart arms 39, 40 which extend from the head 37 towards the intermediate member 34. The arms 39, 40 embrace the intermediate member 34 and are attached pivotally to it in such a way that the wrist head block can rotate relative to the intermediate member about an axis 41. This provides revolute joint 26 of the wrist. Axes 35 and 41 are offset from each other at a substantial angle. Axes 35 and 41 are conveniently transverse to each other, and most conveniently orthogonal to each other. Axes 35 and 41 can conveniently intersect or substantially intersect (e.g. within 50 mm). However, the intermediate member could have some extent so that those axes are offset longitudinally. Axes 35 and 29 are conveniently transverse to each other, and most conveniently orthogonal to each other. Axes 35 and 29 can conveniently intersect or substantially intersect (e.g. within 50 mm). Axes 35 and 29 can conveniently intersect axis 41 at a single point, or the three axes may substantially intersect at a single point (e.g. by all intersecting a sphere of radius 50 mm).

In this way the wrist base block, intermediate member and wrist head block together form a universal joint. The universal joint permits the wrist head block to face any direction in a hemisphere whose base is perpendicular to the axis 29 of joint 28. The linkage between the wrist base block and the wrist head block could be constituted by other types of mechanical linkage, for example by a ball joint or a constant velocity joint. Preferably that linkage acts generally as a spherical joint, although it need not permit relative axial rotation of the wrist base block and the wrist head block since such motion is accommodated by joints 28 and 38. Alternatively, joints 26, 27 and 28 could be considered collectively to form a spherical joint. That spherical joint could be provided as a ball joint. It will be appreciated that the wrist of FIG. 3 has a kinematic redundancy. The instrument 11 could be placed in a wide range of locations in a hemisphere about axis 29 merely by motion of joints 28 and 27. However, it has been found that the addition of joint 26 greatly improves the operation of the robot for surgical purposes by eliminating the kinematic singularity that results from joint pair 28, 27 alone and by simplifying the mechanism of moving the end effector within the patient so that multiple robot arms can work more closely with each other, as will be described in more detail below.

A terminal unit 42 is attached to the head 37 of the wrist head block by revolute joint 38. Joint 38 permits the terminal unit to rotate relative to the head block about an axis 43. Axes 43 and 41 are conveniently transverse to each other, and most conveniently orthogonal to each other. Axes 35 and 29 can conveniently intersect or substantially intersect (e.g. within 50 mm). Axes 35 and 29 can conveniently intersect axis 41 at a single point, or the three axes may substantially intersect at a single point (e.g. by all intersecting a sphere of radius 50 mm).

Figure 5:
FIG. 5 shows a surgical instrument.

The terminal unit has a connector such as a socket or clip to which surgical instrument 11 can be attached. The surgical instrument is shown in more detail in FIG. 5. The instrument comprises in instrument base 50, an elongate instrument shaft 51, optionally one or more joints 52 and an end effector 53. The end effector could, for example, be a gripper, a pair of shears, a camera, a laser or a knife. The instrument base and the connector of the terminal unit 42 are designed cooperatively so that the instrument base can be releasably attached to the connector with the shaft extending away from the instrument base. Conveniently the shaft extends away from the instrument base in a direction that is transverse to the axis of joint 26 and/or parallel or substantially parallel and/or coaxial or substantially coaxial with axis 43 of joint 38. This means that the end effector has substantial range of movement by virtue of the joints of the wrist, and that the joints of the wrist can be used conveniently to position the end effector. For example, with the elongation of the instrument shaft running along axis 43, joint 38 can be used purely to orientate the end effector without moving part or all of the instrument shaft 51 with a lateral component in a way that could result in disruption to the tissue of a patient through which the shaft has been inserted to reach an operation site. The fact that the elongation of the instrument shaft extends away from the wrist as described above means that the wrist has a degree of articulation that is similar to the wrist of a human surgeon. One result of that is that many surgical techniques practised by humans can readily be translated to motions of this robot arm. This can help reduce the need to devise robot-specific versions of known surgical procedures. The shaft is conveniently formed as a substantially linear, rigid rod.

In the description above, the length of the wrist base block 30 is less than that of the final shaft section 21 of the robot arm. This is advantageous because it reduces the mass that needs to be rotated at joint 28. However, joint 28 could be located closer to joint 25 than to joints 26 and 27.

Each joint of the arm can be driven independently of the other joints by one or more motive devices such as electric motors or hydraulic pistons. The motive device(s) could be located locally at the respective joint, or it/they could be located closer to the base of the robot and coupled to the joints by couplings such as cables or linkages. The motive devices are controllable by a user of the robot. The user could control the motive devices in real time by one or more artificial input devices, such as joysticks, or by inputs derived from sensors acting on a replica arm that is moved by the user. Alternatively, the motive devices could be controlled automatically by a computer that has been pre-programmed to perform a surgical procedure. The computer could be capable of reading a computer-readable memory that stores a non-volatile program executable by the computer to cause the robot arm to perform one or more surgical procedures.

Figure 6:
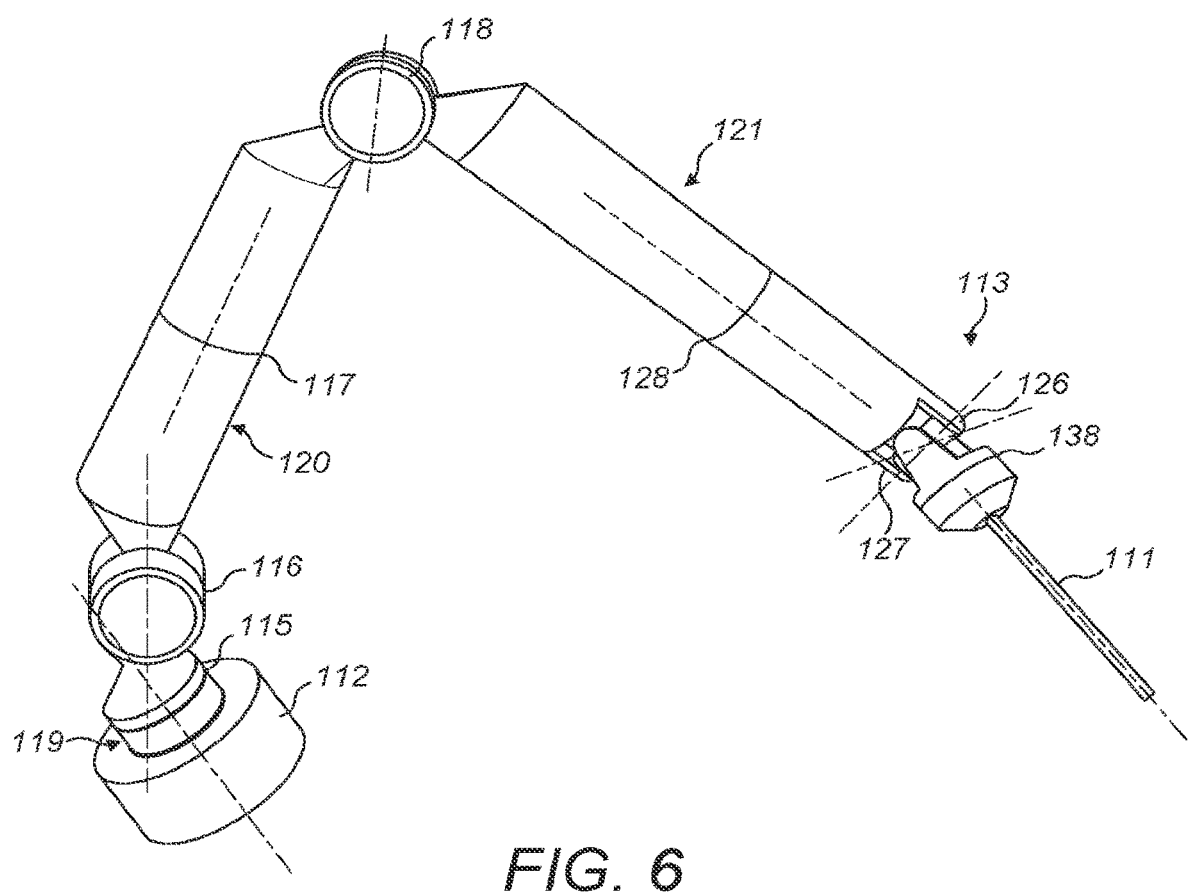
FIG. 6 shows an alternative design of robot arm.

FIG. 6 shows an alternative design of surgical arm. The arm of FIG. 6 comprises a base 112, four joints 115, 116, 117, 118, three shaft sections 119, 120, 121 and a wrist unit 113. The joints are revolute joints. The shaft sections are rigid, with the exception of joints 115 and 117. A surgical instrument 111 is attached to the terminal part of the wrist unit.

The first shaft section 119 extends from the base 112 and comprises joint 115. The first shaft section 119 is attached to the second shaft section 120 by joint 116. The second shaft section 120 comprises joint 117. The second shaft section is attached to the third shaft section 121 by joint 118. The third shaft section 121 terminates in a revolute joint 128 whereby it is attached to the wrist unit 113. The wrist unit comprises an intermediate pair of revolute joints 126, 127, which together constitute a universal joint, and a terminal revolute joint 138.

As with the analogous joints in the robot arm of FIG. 3, the axes of each of the following pairs of joints may independently be transverse to each other, substantially orthogonal to each other (e.g. within any of 30°, 20° or 10° of being orthogonal) or orthogonal to each other: 115 and 116, 116 and 117, 117 and 118, 118 and 128, 128 and 126, 128 and 127, 126 and 138, 127 and 138, 126 and 127. As with the analogous joints in the robot arm of FIG. 3, the axes of the following joints may independently be aligned with (e.g. within any of 30°, 20° or 10° of) or parallel with the principal axis of elongation of the shaft in or on which they are set: joint 117 (with shaft section 120), joint 128 (with shaft section 121). As with the analogous joints in the robot arm of FIG. 3, the wrist may be configured such that the axes of joints 128 and 138 can in one or more configurations of the arm be aligned. Conveniently that alignment may happen when the wrist is in the mid-range of its side-to-side movement. As with the analogous joints in the robot arm of FIG. 3, conveniently the axis of elongation of the instrument 111 may be aligned with (e.g. within any of 30°, 20° or 10° of) or parallel with the axis of joint 138. The axis of elongation of the instrument may be coincident with the axis of joint 138.

The robot arm of FIG. 6 differs from that of FIG. 3 in that the arm sections 119, 120, 121 are configured so that the axis of joint 116 has a substantial lateral offset from the axes of joints 115 and 117 and so that the axis of joint 118 has a substantial lateral offset from the axes of joints 116 and 118. Each of those offsets may independently be, for example, greater than 50 mm, 80 mm or 100 mm. This arrangement is advantageous in that it increases the mobility of the arm without increasing the swept volume close to the tip of the instrument.

In the robot arm of FIG. 6 the axis of the revolute joint closest to the base (joint 115) is fixed at a substantial offset from vertical, e.g. by at least 30°. This may be achieved by fixing the base in an appropriate orientation. If the arm is set up so that the axis of joint 115 is directed generally away from the end effector, as illustrated in FIG. 6, this reduces the chance of a kinematic singularity between joint 115 and joint 117 during an operation.

Thus the arm of FIG. 6 has a number of general properties that can be advantageous in a surgical robot arm.

It comprises a series of revolute joints along its length that include a series of four joints in order along the arm that alternate between (a) having an axis that runs generally towards the next joint in the sequence (a "roll joint") and (b) having an axis that runs generally transverse to the axis of the next joint in the sequence (a "pitch joint"). Thus the arm of FIG. 6 includes roll joints 115 and 117 and pitch joints 116 and 118. This series of joints can provides the arm with a high degree of mobility without the arm needing to be heavy or bulky or to comprise an excessive number of joints. As indicated above, alternate joints can usefully be offset laterally from each other.

It comprises a wrist section commencing at a roll joint (128) and having two pitch joints (126, 127). The pitch joints of the wrist can be co-located such that their axes intersect in all configurations of the arm. This series of joints can provide the end effector with a high degree of mobility about the end of the arm.

A wrist section that terminates in a revolute joint (138) whose axis is coincident with the axis of extension of the surgical instrument. Most conveniently the instrument shaft is elongated linearly and the axis of that joint is aligned with the shaft. This arrangement can permit the end effector to be readily rotated to a desired orientation through motion at a single joint without excessively disrupting a wound channel in the patient. It can also reduce the need for a joint performing an equivalent function in the instrument itself.

A proximal revolute joint (115) that is substantially offset from vertical and most conveniently directed away from the site of the operation in the patient. This reduces the chance of that joint having a kinematic singularity with another joint of the arm.

Figure 7:
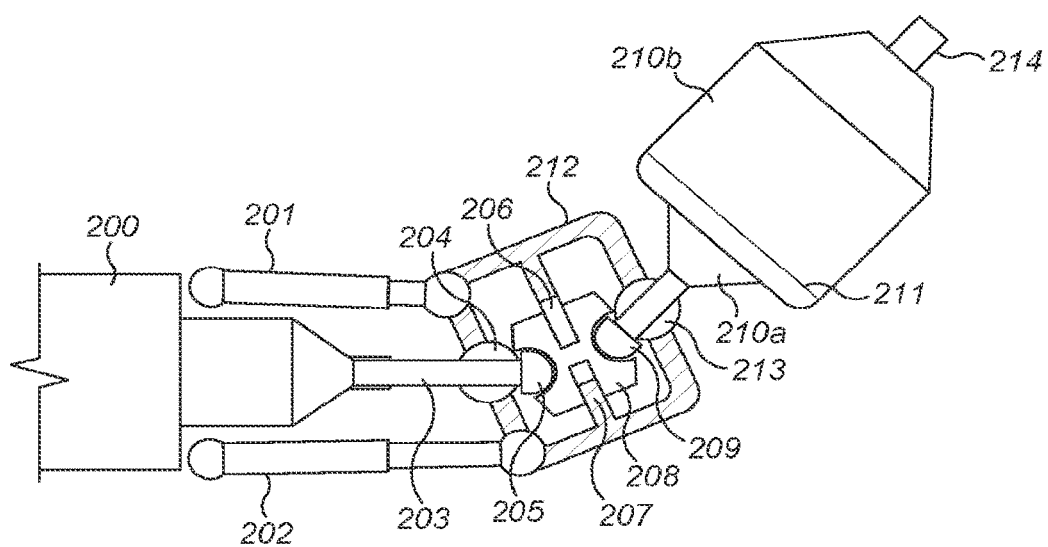
FIG. 7 show an alternative design of wrist.

FIG. 7 shows an alternative design of joint that can be used as a wrist joint in an arm such as those of FIGS. 3 and 6.

In FIG. 7 a shaft section of the arm is shown at 200. That could, for example, be shaft section 21 of FIG. 3, a shaft section connected by a revolute joint to shaft section 21 of FIG. 3, or shaft section 113 of FIG. 6. A number of linear actuators are arranged around the central longitudinal axis of the shaft section 200. The linear actuators are circumferentially offset around the central axis. They could be spaced regularly around the central axis. There could be two, three, four or more such linear actuators. In the example of FIG. 7 there are four linear actuators regularly spaced about the central axis, of which two (201, 202) are visible in FIG. 7. The others have been omitted for clarity. Each linear actuator is coupled by a spherical joint to the distal end of the shaft section 200 from which it protrudes. Instead of linear actuators, other mechanisms capable of applying a force to draw two end-points together or apart could be used. Examples of suitable mechanisms include piston/cylinder arrangements, linear motors and driven compass-like mutually rotatable arms. One end-point of each linear actuator is attached to the spherical joint by which it is attached to the shaft section 200. The other end-point of each linear actuator is attached to another spherical joint by which the linear actuator is attached to an intermediate member 212.

A guide rod 203 is rigidly attached to and extends out of the arm section 200. At its distal end the guide rod terminates in a spherical joint 205 with a follower element 208. The follower 208 is captive inside the intermediate member 212. The follower is constrained to translate only in a single plane relative to the intermediate member. This may be achieved by the follower 208 having a circumferential groove 206 which makes a snug sliding fit over an annular wall 207 that is rigidly attached to and extends radially inwardly within a cavity inside the intermediate member 212.

Along the shaft of the guide rod is a sliding spherical joint 204 with the intermediate member itself. The sliding spherical joint 204 is constituted by a ball through which the shaft of the guide rod can slide. The outer surface of the ball forms a spherical joint with the intermediate member 212. In conjunction with the planarly-constrained motion of the follower 208 with respect to the intermediate member 204 and spherical joint 205 between the distal end of the guide rod and the follower, this joint 204 holds the intermediate member in place whilst enabling it to rotate relative to the shaft section 200 about joint 205. That rotational motion can be driven by the linear actuators, e.g. 201, 202.

On the distal side of the follower, a second guide rod engages the follower through a spherical joint 213. A sliding spherical joint 213 which is similar to joint 204 permits the intermediate member 212 to rotate relative to the second guide rod, and to move linearly relative to the second guide rod along its axis.

A terminal arm piece 210 is rigidly attached to the second guide rod.

The action of the mechanism shown in FIG. 7 permits the terminal arm piece to undergo a generally rotational motion with respect to the shaft section 200 about two orthogonal axes around the region between joints 205, 209. This motion can be driven by the linear actuators. They may operate under the control of a control device, as for the motors discussed above. Alternatively the linear actuators could be driven by hydraulic or pneumatic pressure, through pressure lines that could run from the base of the arm. The nature of the joint constituted by the intermediate member 212 means that the follower 208 tends to exaggerate the angular displacement of the terminal arm piece, allowing considerable angular deviations of the terminal arm piece to be readily achieved.

The terminal arm piece could be a unitary member. Alternatively it could be constituted by two distinct parts 210a and 210b which can rotate relative to each other about a revolute joint 211 akin to joint 138 of FIG. 7. A surgical tool shown partially at 214 could be attached to the terminal arm piece.

As discussed above, the proximal series of joints in the arms of FIGS. 3 and 6 in order towards the distal end of the arm are, using the terms defined above, roll, pitch, roll and pitch joints. This series of joints may be denoted RPRP, where "R" denotes a roll joint, "P" denotes a pitch joint and the joints are listed in series from the proximal towards the distal end of the arm. Using the same terminology, other convenient joint sequences for surgical arms include the following:

1. PRPRP: i.e. the joint sequence of the robot arm of FIGS. 3 and 6 but with an additional pitch joint between the RPRP joint sequence and the base.

2. RPRPR: i.e. the joint sequence of the robot arm of FIGS. 3 and 6 but with an additional roll joint between the RPRP joint sequence and the wrist.

3. RPRPRP: i.e. a series of three RP pairs in succession, akin to the joint sequence of the robot arm of FIGS. 3 and 6 but with an additional pitch joint between the RPRP joint sequence and the base and an additional roll joint between the RPRP joint sequence and the wrist.

Further joints could be added to the arm.

Each of these arms could have a wrist of the type shown in FIG. 3 or 7. One of the joints 28, 38 could be omitted from the wrist.

As indicated above, the surgical instrument may have one or more joints 52 near its tip. If the robot arm is of the type described herein then the surgical instrument may conveniently include only two joints. They can conveniently be revolute joints whose axes run transversely to the instrument shaft 51. The axes of those joints could intersect, forming a universal joint, or could be offset in the direction of elongation of the instrument shaft. The joints of the instrument could be driven by motive means in the arm, and the motion transmitted to the joints through cables or linkages in the instrument. The connector in the terminal part of the wrist unit and the instrument base 50 may be configured to provide for transmitting such motion into the instrument. Conveniently the joints on the instrument do not include a revolute joint whose axis is aligned with the shaft of the instrument. The motion that would be provided by such a joint can conveniently be served by the joint 38 on the wrist of the robot arm. In many surgical procedures such motion is not needed. The instruments are often intended to be disposable; therefore cost can be reduced by omitting such a joint from the instrument. Omitting such a joint also simplifies the mechanical interaction needed between the instrument and the arm since motion for that joint need not be transmitted into the instrument.

In operational use, the robot arm could be covered by a sterile drape to keep the arm separated or sealed from the patient. This can avoid the need to sterilise the arm before surgery. In contrast, the instrument would be exposed on the patient's side of the drape: either as a result of it extending through a seal in the drape or as a result of the drape being sandwiched between the connector in the terminal part of the wrist unit and the instrument base 50. Once the instrument has been attached to the arm it can be used to perform an operation. In performing an operation the arm can first be manipulated so that the axis of the instrument shaft 51 is aligned with the axis between a desired entry point on the exterior of the patient (e.g. an incision in the patient's skin) and the desired operation site. Then the robot arm can be manipulated to insert the instrument through the incision and onwards in a direction parallel to the axis of the instrument shaft until the end effector reaches the operation site. Other tools can be inserted in a similar way by other robot arms. Once the required tools are at the operation site the operation can be conducted, the tools can be withdrawn from the patient's body and the incision(s) can be closed, e.g. by suturing. If it is desired to move the end effector in a direction transverse to the axis of the instrument shaft when the instrument is located in the patient, such motion is preferably performed by rotating the instrument shaft about a centre of motion located at the incision through which the instrument is passing. This avoids making the incision bigger.

A robot arm of the type described above can provide a range of advantages for performing surgical procedures. First, because it does not include an excessive number of joints whist still providing the range of motion needed to position the instrument as a whole and particularly the end effector of the instrument in a wide range of locations and orientations the robot arm can be relatively slim and lightweight. This can reduce the chance of a human being injured through undesired motion of the arm, e.g. when nurses are working around the arm when an operating theatre is being set up to receive a patient. It can also improve the accessibility of multiple such arms to an operation site, especially a site for a procedure such as an ENT (ear, nose and throat) procedure where typically multiple instruments must access the operation site through a small opening. Similar considerations arise in, for example, abdominal procedures where it is common for multiple instruments to enter the patient from a region near the umbilicus and to extend internally of the ribcage into the abdomen of the patient; and in procedures in the pelvic area where the direction in which instruments can approach the operation site is limited by the need to avoid the pelvic bone and other internal structures. Similarly, an arm having improved range of motion can make it easier to position the bases of multiple robots around an operating site because surgical staff have more freedom over where to locate the robot bases. This can help to avoid the need to redesign existing operating room workflows to accommodate a robot. Second, the arm provides sufficient redundant motion that surgical staff have flexibility in positioning the base of the robot relative to the patient. This is important if multiple robots need to work at a small surgical site, if there is additional equipment in the operating theatre or if the patient is of an unusual dimension. Third, when the wrist section comprises a roll joint located proximally of a pair of crossed-axis pitch joints, as in FIG. 4, and particularly if in addition the arm and the instrument are configured so that the instrument shaft extends directly away from those pitch joints, then the motion of the wrist is close to that of a human, making it easier to translate conventional surgical procedures so that they can be performed by the robot. This relationship between the wrist and the instrument also assists in enabling multiple arms to closely approach each other near a surgical site since the terminal sections of the main arm members (e.g. 21 and 121) can be angled relative to the instrument shaft without compromising the freedom of motion of the instrument shaft. This is in part because when the end effector needs to be moved within the patient by rotation about a centre located at the external point of entry of the instrument shaft into the patient, that rotation can in a preferred embodiment of the present arm be provided exclusively by the wrist, without being hindered by kinematic singularities or complex interactions between multiple joints having spatially offset axes, whilst the remainder of the arm merely translates the wrist to the required location. When the robot is under computer control the program for the computer may be defined so as to cause the robot to translate the location of the end effector by rotation of the end effector about a point along the shaft of the instrument. That point may be coincident with or distal of the incision into the patient. The program may be such as to achieve the said translation of the end effector by commanding the motive driver(s) for the wrist to cause joints 26 and/or 27 to rotate the instrument about the point and by simultaneously commanding the motive driver(s) for the remainder of the arm to cause the wrist to translate.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed:

1. A robot arm, the arm having a terminal portion comprising:
    a distal segment having a single connector located on a first axis, the connector being configured to detachably attach a surgical instrument having one or more joints to the distal segment;
    an intermediate segment;
    a basal segment whereby the terminal portion is attached to a remainder of the robot arm;
    a first articulation between the distal segment and the intermediate segment, the first articulation permitting relative rotation of the distal segment and the intermediate segment about the first axis; and
    a second articulation between the intermediate segment and the basal segment, the second articulation permitting relative rotation of the intermediate segment and the basal segment about a second axis; wherein:
    the intermediate segment comprises a third articulation permitting relative rotation of the distal segment and the basal segment about third and fourth axes;
    the first, second and third articulations are arranged such that in a straight configuration of the terminal portion:
        the first and second axes are collinear;
        the third and fourth axes are transverse to each other;
        the third and fourth axes are transverse to the first axis; and
        the third and fourth axes intersect each other,
    and wherein the robot arm is a surgical robot arm.

2. A robot arm as claimed in claim 1, wherein the connector is fixed relative to the distal segment such that it maintains a fixed relative orientation between the distal segment and the instrument.

3. A robot arm as claimed in claim 1, wherein the first articulation is a revolute joint, and the second articulation is a revolute joint.

4. A robot arm as claimed in claim 1, wherein the third articulation is a spherical joint or a pair of revolute joints.

5. A robot arm as claimed in claim 4, wherein the third articulation is a universal joint.

6. A robot arm as claimed in claim 1, wherein the connector for the surgical instrument is only articulable relative to the basal segment using the first, second and third articulations.

7. A robot arm as claimed in claim 1, comprising a surgical instrument attached to the connector.

8. A robot arm as claimed in claim 1, wherein the connector is configured to detachably attach the surgical instrument to the distal segment such that the surgical instrument extends in a direction substantially along the first axis.

9. A robot arm as claimed in claim 1, wherein the robot arm comprises:
    a base; and
    a proximal portion extending between the base and the basal segment of the terminal portion of the arm, the proximal portion being articulated along its length and being rigidly connected to the basal segment.

10. A robot arm as claimed in claim 9, wherein the proximal portion comprises:
a first arm segment;
a second arm segment coupled to the first arm segment by a first arm articulation whereby the second arm segment can rotate relative to the first arm segment about a first arm axis;
a third arm segment coupled to the second arm segment by a second arm articulation whereby the third arm segment can rotate relative to the second arm segment about a second arm axis;
a fourth arm segment coupled to the third arm segment by a third arm articulation whereby the fourth arm segment can rotate relative to the third arm segment about a third arm axis; and
a fifth arm segment coupled to the fourth arm segment by a fourth arm articulation whereby the fifth arm segment can rotate relative to the fourth arm segment about a fourth arm axis; wherein
the second arm axis is transverse to the first arm axis, the third arm axis is transverse to the second arm axis and the fourth arm axis is transverse to the third arm axis; and
the fourth and third arm segments together form an elongate limb that extends in a direction along the third arm axis.

11. A robot arm as claimed in claim 10, wherein the first, second, third and fourth arm articulations are revolute joints, and the fifth arm segment is only articulable relative to the base using the first, second, third and fourth arm articulations.

12. A robot arm as claimed in claim 10, wherein the base is arranged such that the first arm axis is offset from vertical by at least 20°.

13. A robot arm as claimed in claim 10, wherein the fifth arm segment is rigidly attached to the basal segment of the terminal portion of the arm, and the fifth arm segment and the basal segment together form an elongate limb that extends in a direction along the second axis.

14. A robot arm as claimed in claim 13, wherein the second axis is transverse to the fourth arm axis.

15. A robot arm as claimed in claim 13, wherein the fourth arm axis is offset from the second axis in a direction perpendicular to the second axis.

16. A robot arm as claimed in claim 9, wherein the base is directly mountable to the floor or ceiling of an operating theatre or to a mobile trolley or cart.

17. A robot arm as claimed in claim 1, wherein the third articulation is constituted by a joint having an intermediate member capable of moving about a first spherical joint with respect to the basal segment and about a second spherical joint with respect to the distal segment, the first and second spherical joints being constrained to move in a plane with respect to the intermediate member.

18. A robot arm as claimed in claim 1, wherein the robot arm is configured to perform surgical tasks.

* * * * *